United States Patent
Kaminosono et al.

(10) Patent No.: US 11,560,478 B2
(45) Date of Patent: Jan. 24, 2023

(54) DENTAL ADDITION SILICONE IMPRESSION MATERIAL

(71) Applicant: GC Corporation, Shizuoka (JP)

(72) Inventors: Yoshiya Kaminosono, Tokyo (JP); Kyousuke Hirano, Tokyo (JP)

(73) Assignee: GC Corporation, Shizuoka (JP)

( * ) Notice: Subject to any disclaimer, the term of this patent is extended or adjusted under 35 U.S.C. 154(b) by 0 days.

(21) Appl. No.: 17/261,284

(22) PCT Filed: Apr. 19, 2019

(86) PCT No.: PCT/JP2019/016837
§ 371 (c)(1),
(2) Date: Jan. 19, 2021

(87) PCT Pub. No.: WO2020/021795
PCT Pub. Date: Jan. 30, 2020

(65) Prior Publication Data
US 2021/0277240 A1    Sep. 9, 2021

(30) Foreign Application Priority Data

Jul. 26, 2018  (JP) .............................. JP2018-140415

(51) Int. Cl.
*C08L 83/04*  (2006.01)
*A61K 6/90*  (2020.01)

(52) U.S. Cl.
CPC ................ *C08L 83/04* (2013.01); *A61K 6/90* (2020.01); *C08L 2203/02* (2013.01)

(58) Field of Classification Search
CPC ....................................................... A61K 6/90
See application file for complete search history.

(56) References Cited

U.S. PATENT DOCUMENTS

| 5,684,060 A * | 11/1997 | Konings | ............... C08L 83/04 |
| | | | 264/16 |
| 2002/0193502 A1* | 12/2002 | Hare | ..................... A61K 6/90 |
| | | | 524/588 |
| 2010/0069525 A1* | 3/2010 | Kamohara | ............. A61K 6/90 |
| | | | 523/109 |
| 2010/0292362 A1* | 11/2010 | Zech | ..................... A61K 6/887 |
| | | | 523/109 |

FOREIGN PATENT DOCUMENTS

| JP | H10-072307 | 3/1998 |
| JP | 2009-203196 | 9/2009 |
| JP | 2010-070643 | 4/2010 |
| WO | WO-2017095405 A1 * | 6/2017 ............. A61K 8/042 |

OTHER PUBLICATIONS

International Search Report for PCT/JP2019/016837 dated Jun. 11, 2019.

* cited by examiner

*Primary Examiner* — Michael F Pepitone
(74) *Attorney, Agent, or Firm* — IPUSA, PLLC

(57) ABSTRACT

The present invention relates to a dental addition silicone impression material containing: an organopolysiloxane; and a nonionic surfactant, wherein the organopolysiloxane contains M units represented by the formula: $R_3SiO_{1/2}$, in which R is a substituted or an unsubstituted alkyl group, a substituted or an unsubstituted aryl group, a substituted or an unsubstituted aralkyl group, a substituted or an unsubstituted alkoxy group or hydroxy group, and three R's are identical or different, and Q units represented by the chemical formula: $SiO_2$.

4 Claims, No Drawings

DENTAL ADDITION SILICONE IMPRESSION MATERIAL

CROSS-REFERENCE TO RELATED APPLICATIONS

The present application is a national-phase application of the international application No. PCT/JP2019/016837 filed on Apr. 19, 2019, which is based on and claims priority to the Japanese patent application No. 2018-140415 filed on Jul. 26, 2018, the entire contents of which are incorporated herein by reference.

FIELD OF THE INVENTION

The present invention relates to a dental addition silicone impression material.

BACKGROUND OF THE INVENTION

In the dental field, dental addition silicone impression materials are widely used to obtain dental impressions.

However, a kneaded mixture of addition silicone impression material has a problem that a precise impression cannot be obtained because of its low hydrophilicity.

Patent document 1 discloses a hydrophilic organopolysiloxane composition for a hydrosilylation reaction curable dental impression material, which consists of polyether, includes: (A) a diorganopolysiloxane having 0.1 or more of alkenyl groups bonded to a silicon atom in one molecule; (B) a composition represented by the following formula (1):

$$R_p SiO_{(4-p)/2} \tag{1},$$

wherein, R is an unsubstituted or a substituted of the same or different monovalent hydrocarbon group, an alkoxy group or a hydroxyl group, 0.1 to 80% by mol of all R is an alkenyl group, and p is a positive number satisfying $1 \leq p < 2$, a liquid or solid organopolysiloxane having $SiO_2$ units and $R_3SiO_{1/2}$ units in its composition and having a viscosity at 23° C. of 10 mPa·s or more; (C) an organohydrogenpolysiloxane having 2 or more of hydrogen atoms bonded to a silicon atom in one molecule; (D) a hydrosilylation catalyst, (E) a composition represented by the following formula (2):

$$R^1 O(C_2H_4O)_m(C_3H_6O)_n R^1 \tag{2},$$

wherein, $R^1$ represents a group represented by $C_3H_6SiR^2_k(OR^2)_{3-k}$ ($R^2$ represents a monovalent hydrocarbon group, k represents 0, 1, 2 or 3), or a monovalent hydrocarbon group, and a plurality of $R^1$ and $R^2$ may be the same or different from each other, and at least two of $R^1$ and $R^2$ may be an alkenyl group, m is an integer of 0 to 100, n is an integer of 0 to 350, and m+n is an integer of 3 to 350).

RELATED-ART DOCUMENT

Patent Documents

Patent Document 1: Japanese Patent Application Laid-Open 2010-70643

SUMMARY OF THE INVENTION

Problems to be Solved by the Invention

Accordingly, a hydrophilcity of a kneaded mixture of organopolysiloxane composition for a hydrosilylation reaction curable dental impression material is needed to further improve.

One aspect of the invention is to provide a dental addition silicone impression material capable of having improved the hydrophilicity in a kneaded mixture.

Means for Solving the Problems

One aspect of the present invention includes a dental addition silicone impression material containing: an organopolysiloxane; and a nonionic surfactant, wherein the organopolysiloxane contains M units represented by the formula: $R_3SiO_{1/2}$, in which R is a substituted or an unsubstituted alkyl group, a substituted or an unsubstituted aryl group, a substituted or an unsubstituted aralkyl group, a substituted or an unsubstituted alkoxy group or hydroxy group, and three R's are identical or different, and Q units represented by the chemical formula: $SiO_2$.

Effects of the Invention

According to one aspect of the present invention, a dental addition silicone impression material can be provided that is capable of improving the hydrophilicity of a kneaded mixture.

DETAILED DESCRIPTION OF THE INVENTION

Next, an embodiment for carrying out the present invention will be described.

[Dental Addition Silicone Impression Material]

A dental addition silicone impression material of the present embodiment contains an organopolysiloxane (A) and a nonionic surfactant (B), thereby improving a hydrophilicity of a kneaded mixture.

When a dynamic wettability test is used for evaluating the hydrophilicity of a kneaded mixture of a dental addition silicone impression material, the hydrophilicity of the kneaded mixture of the dental addition silicone impression material can be evaluated under conditions close to clinical conditions, because the amount of water with respect to the kneaded mixture of the dental addition silicone impression material is higher in comparison to when the hydrophilicity is evaluated using a contact angle meter.

[Organopolysiloxane (A)]

An organopolysiloxane (A) contains M units and Q units. Where the M units are represented by the following general formula:

$$R_3SiO_{1/2}$$

wherein R is a substituted or an unsubstituted alkyl group, a substituted or an unsubstituted aryl group, a substituted or an unsubstituted aralkyl group, a substituted or an unsubstituted alkoxy group or hydroxy group, and three R's are identical or different. Also, the Q units are represented by the following chemical formula:

$$SiO_2.$$

The number of carbons of the alkyl group, aryl group, and aralkyl group in the R is usually about 1 to 12 carbons and preferably about 1 to 8 carbons.

Examples of the alkyl groups in the R include a methyl group, ethyl group, propyl group, isopropyl group, butyl group, isobutyl group, tert-butyl group, pentyl group, neopentyl group, hexyl group, cyclohexyl group, octyl group, nonyl group, decyl group, and the like.

Examples of aryl groups in the R include a phenyl group, tolyl group, xylyl group, naphthyl group, and the like.

Examples of the aralkyl groups in the R include a benzyl group, phenylethyl group, phenylpropyl group, and the like.

Examples of substituents in the R include halogen atoms such as fluorine atom, bromine atom, chlorine atom, and the like; cyano group; and the like.

Examples of alkyl groups substituted by substituents include a chloromethyl group, chloropropyl group, bromoethyl group, trifluoropropyl group, cyanoethyl group, and the like.

As the R, a methyl group is particularly preferably used in view of compatibility with an organopolysiloxane and an organohydrogenpolysiloxane having alkenyl group as described below.

The organopolysiloxane (A) includes Q units and M units, but may further include D units and/or T units.

Here, the D units are represented by the following general formula:

$R_2SiO$, and the T units are represented by the following general formula:

$RSiO_{3/2}$

In addition, R in the D units and the T units are the same as R in the M units.

The organopolysiloxane (A) is preferably a trimethylsiloxysilicate.

Examples of commercially available trimethylsiloxysilicates include KF-7312K (manufactured by Shin-Etsu Chemical Co., Ltd.) and the like.

Note that, two or more kinds of organopolysiloxane (A) may be used in combination.

The content of the organopolysiloxane (A) in the dental addition silicone impression material of the present embodiment is preferably 1% by mass or more and 60% by mass or less, more preferably 3% by mass or more and 50% by mass or less, with respect to the total amount of the organopolysiloxane having alkenyl group and the organohydrogenpolysiloxane described below. When the content of the organopolysiloxane in the dental addition silicone impression material of the present embodiment is 2% by mass or more with respect to the total amount of the organopolysiloxane having alkenyl group and the organohydrogenpolysiloxane, the hydrophilicity of the dental addition silicone impression material is further improved. When the content of the organopolysiloxane in the dental addition silicone impression material of the present embodiment is 60% by mass or less with respect to the total amount of the organopolysiloxane having alkenyl group and the organohydrogenpolysiloxane, a compatibility of the organopolysiloxane (A) with the organopolysiloxane having alkenyl group and the organohydrogenpolysiloxane is improved.

[Nonionic Surfactant (B)]

Examples of nonionic surfactants (B) include silicone-based surfactants, hydrocarbon-based surfactants (e.g., polyoxyethylene alkyl ethers), fluorocarbon-based surfactants, polyethylene glycol-polypropylene glycol block copolymers, and the like. The silicone-based surfactants and hydrocarbon-based surfactants are preferably used.

Examples of commercially available silicone-based surfactants include KF-351A, KF945, KF640, KF642, KF643, KF644 (manufactured by Shin-Etsu Chemical Co., Ltd.), and the like.

Examples of commercially available hydrocarbon-based surfactants include Naroacty CL40, CL50, CL70, CL90, Sannonic SS30, SS50, SS70, SS90 (Sanyo Chemical Ltd.), and the like.

Two or more kinds of nonionic surfactant (B) may be used in combination.

The content of the nonionic surfactant (B) in the dental addition silicone impression material of the present embodiment is preferably 1% by mass or more and 50% by mass or less, and more preferably 3% by mass or more and 30% by mass or less, with respect to the total amount of the organopolysiloxane having alkenyl group and the organohydrogenpolysiloxane described below. When the content of the nonionic surfactant in the dental silicone impression material of the present embodiment is 1% by mass or more with respect to the total amount of the organopolysiloxane having alkenyl group and the organohydrogenpolysiloxane, the hydrophilicity of the dental silicone impression material is further improved. When the content of the nonionic surfactant in the dental silicone impression material of the present embodiment is 50% by mass or less, the preservation stability of the impression improved.

[Other Components]

The dental addition silicone impression material of the present embodiment preferably further contains an organopolysiloxane having alkenyl group, an organohydrogenpolysiloxane, and a hydrosilylation catalyst.

[Organopolysiloxane Having Alkenyl Group]

An organopolysiloxane having alkenyl group is represented by the following average composition formula:

$R^1{}_aSiO_{(4-a)/2}$ wherein $R^1$ is a substituted or unsubstituted monovalent hydrocarbon group having 1 to 10 carbons, preferably 1 to 8 carbons; a is 1.95 to 2.05, preferably 2.00 to 2.02; and for $R^1a$, an alkenyl group having 2 to 8 carbons and preferably 2 to 6 carbons are 0.001 to 20% by mol, preferably 0.001 to 10% by mol.

Here, the monovalent hydrocarbon group in the $R^1$ includes, for example, alkyl groups such as methyl group, ethyl group, propyl group, isopropyl group, butyl group, isobutyl group, tert-butyl group, pentyl group, neopentyl group, hexyl group, cyclohexyl group, octyl group, nonyl group, decyl group, and the like; aryl groups such as phenyl group, tolyl group, xylyl group, naphthyl group, and the like; aralkyl groups such as benzyl group, phenylethyl group, phenylpropyl group, and the like; and alkenyl groups such as vinyl group, and allyl group, propenyl group, isopropenyl group, butenyl group, hexenyl group, cyclohexenyl group, octenyl group, and the like.

Examples of substituents in the $R^1$ include halogen atoms such as fluorine atom, bromine atom, chlorine atom, and the like; cyano group; and the like.

Examples of alkyl groups substituted by substituents include a chloromethyl group, chloropropyl group, bromoethyl group, trifluoropropyl group, cyanoethyl group, and the like.

The alkenyl group may be bonded to a silicon atom at the terminal end or may be bonded to a silicon atom somewhere other than the terminal end, but preferably is bonded to a silicon atom at the terminal end.

Preferably, the $R^1$ other than the alkenyl group is a methyl group or a phenyl group.

Here, the organopolysiloxane having the alkenyl group contains M units and D units, but may further contain T units.

The organopolysiloxane having alkenyl group can also be either a homopolymer or a copolymer.

Examples of the organopolysiloxane having alkenyl group include dimethyl polysiloxane having both ends sealed with a dimethylvinyl siloxy group; dimethyl polysiloxane having both ends sealed with a methyldivinylsiloxy group; a copolymer of dimethylsiloxane (80% by mol) and methylphenylsiloxane (20% by mol) having both ends sealed with a dimethylvinyl siloxy group; a copolymer of dimethylsiloxane (80% by mol) and diphenylsiloxane (20% by mol) having both ends sealed with a dimethylvinyl siloxy group; a copolymer of dimethylsiloxane (90% by mol) and diphenylsiloxane (10% by mol) having both ends sealed with a dimethylvinyl siloxy group; and a copolymer of dimethylsiloxane and methylvinylsiloxane having both ends sealed with a trimethylsiloxy group.

Two or more kinds of organopolysiloxanes having alkenyl group may be used in combination.

[Organohydrogenpolysiloxane]

The organohydrogenpolysiloxane is hydrosilylated with the organopolysiloxane having alkenyl group so that a dental addition silicone impression material can be cured.

The organohydrogenpolysiloxane is represented by the following average composition formula:

wherein $R^2$ is a substituted or unsubstituted monovalent hydrocarbon group of 1 to 10 carbons, b is 0.7 to 2.1, c is 0.001 to 1.0, and b+c is 0.8 to 3.0.

The number of hydrosilyl groups present in the organohydrogenpolysiloxane is preferably 2 to 300, more preferably 3 to 200, and even more preferably 4 to 100.

Here, $R^2$ is similar to $R^1$ of the organopolysiloxane having alkenyl group, but preferably does not include aliphatic unsaturated bond.

Examples of organohydrogenpolysiloxanes include 1,1,3,3-tetramethyldisiloxane, 1,3,5,7-tetramethyl cyclotetrasiloxane, methylhydrogencyclopolysiloxane, methylhydrogensiloxane-dimethylsiloxane cyclic copolymer, tris(dimethylhydrogensiloxy) methylsilane, tris(dimethylhydridrogenesiloxy) phenylsilane, methylhydrogenpolysiloxane having both ends sealed with trimethylsiloxy groups, a copolymer of dimethylsiloxane-methylhydrogensiloxane having both ends sealed with trimethylsiloxy groups, and dimethylpolysiloxane having both ends sealed with dimethylhydrogensiloxy groups, a copolymer of dimethylsiloxane-methylhydrogensiloxane having both ends sealed with dimethylhydrogensiloxy groups, methyl hydrogenpolysiloxane having both ends sealed with dimethylhydrogensiloxy group, a copolymer of methyl hydrogensiloxane-diphenylsiloxane copolymer having both ends sealed with trimethylsiloxy group, a copolymer of methyl hydrogensiloxane-diphenylsiloxane-dimethylsiloxane having both ends sealed with trimethylsiloxy group, a copolymer having $(CH_3)_2HSiO_{1/2}$ units and $SiO_{4/2}$ units, and a copolymer having $(CH_3)_2HSiO_{1/2}$ units, $SiO_{4/2}$ units, and $(C_6H_5) SiO_{3/2}$ units.

The organohydrogenpolysiloxane may be a linear, cyclic, or branched.

The number of silicon atoms present in the organohydrogenpolysiloxane is preferably 2 to 1,000, more preferably 3 to 300, and even more preferably 4 to 100.

Two or more kinds of the organohydrogenpolysiloxane may be used in combination.

A molar ratio of the hydrosilyl group of the organohydrogenpolysiloxane with respect to the alkenyl group of the organopolysiloxane having alkenyl group is 0.1 to 4.0.

[Hydrosilylation Catalyst]

Examples of the hydrosilylation catalyst include platinum black, secondary platinum chloride, platinum chloride acid, a reactant of platinum chloride acid and monohydric alcohol, a complex of platinum chloride acid and olefins, a platinum-based catalyst such as platinum bis-acetoacetate, a palladium-based catalyst, and a platinum-based metal catalyst such as rhodium-based catalyst.

In addition, two or more kinds of hydrosilylation catalysts may be used in combination.

[Filler]

The dental addition silicone impression material of the present embodiment may further contain a filler.

Examples of the filler include aerosol silica particles, wet-type silica particles, crystalline silica particles, carbon black, iron oxide red particles, cerium oxide particles, titanium oxide particles, calcium carbonate particles, aluminum hydroxide particles, titanate particles, and the like.

Two or more kinds of filler may be used in combination.

[Method of Using Dental Addition Silicone Impression Material]

The dental addition silicone impression material of the present embodiment is preferably used as a two-agent type composition in which a hydrosilylation catalyst and an organohydrogenpolysiloxane are separated.

As an example, a kneaded mixture of a first agent containing a hydrosilylation catalyst and a second agent containing an organohydrogenpolysiloxane is built up in a tray or mouth, and left in the mouth until the kneaded mixture hardens.

As another example, a first agent containing a hydrosilylation catalyst and a second agent containing an organohydrogenpolysiloxane are kneaded, molded, and allowed to stand at room temperature or heated to 50 to 200° C.

EXAMPLE

Hereinafter, examples of the present invention will be described, but the present invention is not limited to the described examples.

Examples 1 to 4, Comparative Examples 1 and 2

A paste A and a paste B (addition silicone impression materials) were prepared by mixing a trimethylsiloxysilicate, a nonionic surfactant, a vinyl polysiloxane, an organohydrogenpolysiloxane, silica particles, and a hydrosilylation catalyst in the amounts indicated in Table 1.

The details of each component in Table 1 are as follows.

Trimethylsiloxysilicate (60% by mass): KF-7312K (manufactured by Shin-Etsu Chemical Co., Ltd.) (a mixture with low viscosity dimethicone (40% by mass)

Nonionic surfactant 1: Naroacty CL-40 (manufactured by Sankyo Chemical Inc.) (polyoxyethylene alkyl ether)

Nonionic surfactant 2: KF-644 (manufactured by Shin-Etsu Chemical Co., Ltd.) (Silicone-based surfactant)

Vinyl polysiloxane: dimethyl polysiloxane having both ends sealed with vinyl dimethylsiloxy groups (viscosity: 4,000 mPa·s)

Organohydrogenpolysiloxane: a copolymer of dimethylsiloxane-methylhydrogensiloxane having both ends sealed with trimethylsiloxy groups (33% by mass of hydrogen atom bonded to silicon atom, viscosity: 10 mPa·s)

Silica particles: CRYSTALITE 5X (manufactured by Tatsumori, Ltd.)

Hydrosilylation catalyst: toluene solution of platinum 1,3-divinyl-1,1,3,3-tetramethyldisiloxane complex (0.5% by mass of platinum)

[Hydrophilicity of Addition Silicone Impression Materials]

The hydrophilicity of the addition silicone impression materials was evaluated using a dynamic wetting tester WET-6000 (manufactured by Rhesca Corporation). Specifically, the paste A and paste B were started to be kneaded, then one minute later, the measurement of a surface tension of the addition silicone impression material with respect to water was initiated. The measurement value of 5 seconds after the start of the measurement was considered as the surface tension.

Table 1 indicates the results of the evaluation of the hydrophilicity of the addition silicone impression materials.

TABLE 1

| | Examples | | | | | | | | Comparative Examples | | | |
|---|---|---|---|---|---|---|---|---|---|---|---|---|
| | 1 | | 2 | | 3 | | 4 | | 1 | | 2 | |
| Paste | A | B | A | B | A | B | A | B | A | B | A | B |
| Trimethylsiloxysilicate (60% by mass) | 8 | 8 | 8 | 8 | 8 | 8 | 3 | 3 | | | 8 | 8 |
| Nonionic surfactant 1 | | 10 | | 10 | | | | 10 | | 10 | | |
| Nonionic surfactant 2 | | | | | | | | | | | | |
| Vinyl polysiloxane | 37 | 22 | 42 | 27 | 37 | 22 | 42 | 27 | 50 | 35 | 37 | 32 |
| Organohydrogenpolysiloxane | | 5 | | 5 | | 5 | | 5 | | 5 | | 5 |
| Silica particles | 55 | 55 | 50 | 50 | 55 | 55 | 55 | 55 | 50 | 50 | 55 | 55 |
| Hydrosilylation catalyst | Amount of catalyst | | Amount of catalyst | | Amount of catalyst | | Amount of catalyst | | Amount of catalyst | | Amount of catalyst | |
| Total | 100 | 100 | 100 | 100 | 100 | 100 | 100 | 100 | 100 | 100 | 100 | 100 |
| Surface tension with respect to water [mN/m] | 0.40 | | 0.25 | | 0.20 | | 0.10 | | −0.10 | | −0.30 | |

From Table 1, it can be seen that the kneaded mixtures of the addition silicone impression materials in Examples 1 to 4 had high surface tension with respect to water and high hydrophilicity.

In contrast, the kneaded mixture of the addition silicone impression material in Comparative Example 1 had low surface tension with respect to water and low hydrophilicity, because the kneaded mixture did not contain the organopolysiloxane (A).

Further, the kneaded mixture of the addition silicone impression material in Comparative Example 2 had low surface tension with respect to water and low hydrophilicity, because the kneaded mixture did not contain the nonionic surfactant (B).

The invention claimed is:

1. A dental addition silicone impression material comprising:
   an organopolysiloxane;
   an organohydrogenpolysiloxane;
   a hydrosilylation catalyst; and
   a nonionic surfactant, wherein the organopolysiloxane contains
   M units represented by the formula:

$R_3SiO_{1/2}$, in which R is a substituted or an unsubstituted alkyl group, a substituted or an unsubstituted aryl group, a substituted or an unsubstituted aralkyl group, a substituted or an unsubstituted alkoxy group or hydroxy group, and three R's are identical or different, and
   Q units represented by the chemical formula:

$SiO_2$, wherein the organopolysiloxane is a trimethylsiloxysilicate, and
   wherein the dental addition silicone impression material is a two-agent composition in which the hydrosilylation catalyst and the organohydrogenpolysiloxane are separated.

2. The dental addition silicone impression material according to claim 1, further comprising D units represented by the formula: $R_2SiO$ or T units represented by the formula: $RSiO_{3/2}$ or both, wherein R in the D units and the T units are the same as R in the M units.

3. The dental addition silicone impression material according to claim 1, wherein the nonionic surfactant is selected from silicone-based surfactants, fluorocarbon-based surfactants, and polyethylene glycol-polypropylene glycol block copolymers.

4. A dental addition silicone impression material comprising:
   an organopolysiloxane; and
   a nonionic surfactant,
   wherein the organopolysiloxane consists of M units and Q units,
   wherein the M units are represented by the formula:

$R_3SiO_{1/2}$, in which R is a substituted or an unsubstituted alkyl group, a substituted or an unsubstituted aryl group, a substituted or an unsubstituted aralkyl group, a substituted or an unsubstituted alkoxy group or hydroxy group, and three R's are identical or different,
   wherein the Q units are represented by the chemical formula:

$SiO_2$, and wherein the organopolysiloxane is a trimethylsiloxysilicate.

* * * * *